(12) United States Patent
Ou et al.

(10) Patent No.: US 10,988,421 B2
(45) Date of Patent: Apr. 27, 2021

(54) REMOVAL OF BROMINE INDEX-REACTIVE COMPOUNDS

(71) Applicant: ExxonMobil Chemical Patents Inc., Baytown, TX (US)

(72) Inventors: John Di-Yi Ou, Houston, TX (US); Kevin J. Knob, Fairfield, CA (US); Surbhi Jain, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 367 days.

(21) Appl. No.: 14/522,762

(22) Filed: Oct. 24, 2014

(65) Prior Publication Data
US 2015/0158794 A1    Jun. 11, 2015

Related U.S. Application Data

(60) Provisional application No. 61/912,881, filed on Dec. 6, 2013.

(51) Int. Cl.
*C07C 7/163* (2006.01)
*B01J 21/16* (2006.01)
(Continued)

(52) U.S. Cl.
CPC .............. *C07C 7/163* (2013.01); *B01J 21/06* (2013.01); *B01J 21/12* (2013.01); *B01J 21/16* (2013.01); *B01J 29/7038* (2013.01)

(58) Field of Classification Search
CPC ......... C07C 7/148; C07C 7/163; C07C 7/177; C07C 15/08
See application file for complete search history.

(56) References Cited

U.S. PATENT DOCUMENTS 2,778,863 A    1/1957   Maisel et al.
3,670,041 A    6/1972   Juhl et al.
(Continued)

FOREIGN PATENT DOCUMENTS

WO    WO 2009/061303    5/2009
WO    WO 2011/078810    6/2011
(Continued)

OTHER PUBLICATIONS

Ye Xiaozhou et al. "Industrial Application of HDO-18 selective hydrogenation catalyst" Petroleum Processing and Petrochemicals. 2004. Abstract (Year: 2004).*

*Primary Examiner* — Philip Y Louie
*Assistant Examiner* — Alyssa L Cepluch

(57) ABSTRACT

The invention is directed to the use of dissolved hydrogen in a purification process for the removal of Bromine Index (BI)-reactive compounds from an aromatic-containing hydrocarbon stream derived from various sources, such as petroleum fractionation, reforming, thermal cracking, catalytic cracking, isomerization, transalkylation, alkylation, coking, conversion of oxygenates, conversion of biomass, etc. The purification process comprises contacting the aromatic-containing hydrocarbon stream in the liquid phase in the presence of dissolved hydrogen with at least one suitable catalytic material under conditions effective to provide a product stream having a lower concentration of BI-reactive compounds than the untreated stream.

15 Claims, 1 Drawing Sheet

(51) Int. Cl.
  *B01J 21/06*  (2006.01)
  *B01J 21/12*  (2006.01)
  *B01J 29/70*  (2006.01)

(56) References Cited

U.S. PATENT DOCUMENTS

| | | | |
|---|---|---|---|
| 4,118,429 A * | 10/1978 | Fritsch | C07C 5/2702 |
| | | | 208/143 |
| 4,584,424 A | 4/1986 | Barthomeuf et al. | |
| 4,645,587 A | 2/1987 | Kokayeff et al. | |
| 4,751,346 A | 6/1988 | Barthomeuf et al. | |
| 4,795,550 A | 1/1989 | Sachtler et al. | |
| 4,816,538 A | 3/1989 | Abdo | |
| 4,827,076 A | 5/1989 | Abdo | |
| 4,886,935 A | 12/1989 | Abdo | |
| 4,923,592 A | 5/1990 | Abdo | |
| 4,923,836 A | 5/1990 | Abdo | |
| 5,658,453 A * | 8/1997 | Russ | C10G 69/08 |
| | | | 208/144 |
| 5,821,397 A | 10/1998 | Joly et al. | |
| 5,977,420 A | 11/1999 | Abichandani et al. | |
| 5,998,688 A | 12/1999 | Abichandani et al. | |
| 6,008,425 A | 12/1999 | Mohr et al. | |
| 6,028,238 A | 2/2000 | Beck et al. | |
| 6,368,496 B1 | 4/2002 | Brown et al. | |
| 6,660,896 B1 | 12/2003 | Buchanan et al. | |
| 6,770,792 B2 | 8/2004 | Mohr et al. | |
| 6,797,849 B2 | 9/2004 | McMinn et al. | |
| 6,878,855 B2 | 4/2005 | Deckman et al. | |
| 6,924,405 B2 | 8/2005 | Mohr et al. | |
| 6,977,317 B1 | 12/2005 | Frey et al. | |
| 7,115,538 B2 | 10/2006 | Buchanan et al. | |
| 7,247,762 B2 | 7/2007 | Stern et al. | |
| 7,270,792 B2 | 9/2007 | Deckman et al. | |
| 7,271,118 B2 | 9/2007 | Raich et al. | |
| 7,439,412 B2 | 10/2008 | Ou et al. | |
| 7,626,065 B2 | 12/2009 | Ou et al. | |
| 7,744,750 B2 * | 6/2010 | Brown | C07C 7/13 |
| | | | 208/263 |
| 7,790,020 B2 | 9/2010 | Kokayeff et al. | |
| 7,794,585 B2 | 9/2010 | Leonard et al. | |
| 7,794,588 B2 | 9/2010 | Kokayeff et al. | |
| 7,799,208 B2 | 9/2010 | Kokayeff et al. | |
| 7,959,793 B2 * | 6/2011 | Bakshi | C10G 45/08 |
| | | | 208/208 R |
| 8,216,450 B2 * | 7/2012 | Brown | C07C 7/163 |
| | | | 208/263 |
| 8,221,706 B2 | 7/2012 | Petri et al. | |
| 8,273,934 B2 | 9/2012 | Ou et al. | |
| 8,283,506 B2 | 10/2012 | Kokayeff et al. | |
| 8,350,106 B2 * | 1/2013 | Jan | C07C 2/66 |
| | | | 585/258 |
| 8,399,727 B2 * | 3/2013 | Lattner | C07C 2/864 |
| | | | 585/467 |
| 8,541,639 B2 | 9/2013 | Ou et al. | |
| 8,569,559 B2 | 10/2013 | Ou | |
| 8,692,044 B2 | 4/2014 | Ou et al. | |
| 8,697,929 B2 | 4/2014 | Ou et al. | |
| 8,716,541 B2 | 5/2014 | Ou | |
| 8,835,705 B2 | 9/2014 | Cao et al. | |
| 8,871,082 B2 | 10/2014 | Zimmerman et al. | |
| 9,018,121 B2 | 4/2015 | Ross et al. | |
| 9,227,888 B2 | 1/2016 | Porter et al. | |
| 9,260,360 B2 | 2/2016 | Cao et al. | |
| 9,309,169 B2 | 4/2016 | Ou et al. | |
| 9,457,292 B2 | 10/2016 | Ou | |
| 9,469,578 B2 | 10/2016 | Ou et al. | |
| 2006/0020154 A1 | 1/2006 | Lo et al. | |
| 2006/0270886 A1 | 11/2006 | Brown et al. | |
| 2007/0004956 A1 | 1/2007 | Abdelghani | |
| 2007/0112239 A1 | 5/2007 | Brown et al. | |
| 2008/0023372 A1 | 1/2008 | Leonard et al. | |
| 2008/0194893 A1 * | 8/2008 | Sohn | C07C 6/126 |
| | | | 585/316 |
| 2009/0036724 A1 * | 2/2009 | Negiz | C07C 6/123 |
| | | | 585/470 |
| 2009/0077866 A1 | 3/2009 | Kalnes et al. | |
| 2009/0077867 A1 | 3/2009 | Marker et al. | |
| 2009/0095653 A1 | 4/2009 | Kokayeff et al. | |
| 2009/0193709 A1 | 8/2009 | Marker et al. | |
| 2009/0321310 A1 | 12/2009 | Kokayeff et al. | |
| 2009/0321319 A1 | 12/2009 | Kokayeff et al. | |
| 2009/0326289 A1 | 12/2009 | Petri et al. | |
| 2010/0274064 A1 | 10/2010 | Brown | |
| 2011/0024327 A1 | 2/2011 | Marker et al. | |
| 2011/0046427 A1 | 2/2011 | Negiz et al. | |
| 2011/0319692 A1 | 12/2011 | Spieker et al. | |
| 2012/0074038 A1 | 3/2012 | Petri et al. | |
| 2012/0083638 A1 | 4/2012 | Boldingh et al. | |
| 2012/0090223 A1 | 4/2012 | Kokayeff et al. | |
| 2012/0108867 A1 | 5/2012 | Pilliod et al. | |
| 2012/0108868 A1 | 5/2012 | Pilliod et al. | |
| 2013/0256191 A1 | 10/2013 | Zimmerman et al. | |
| 2013/0259764 A1 | 10/2013 | Zimmerman et al. | |
| 2013/0259765 A1 | 10/2013 | Zimmerman et al. | |
| 2013/0324779 A1 | 12/2013 | Heeter et al. | |
| 2015/0247098 A1 * | 9/2015 | Li | B01F 3/04099 |
| | | | 585/258 |

FOREIGN PATENT DOCUMENTS

| | | | |
|---|---|---|---|
| WO | 2012/050766 A3 | 8/2012 | |
| WO | WO-2014044195 A1 * | 3/2014 | B01J 4/004 |

* cited by examiner

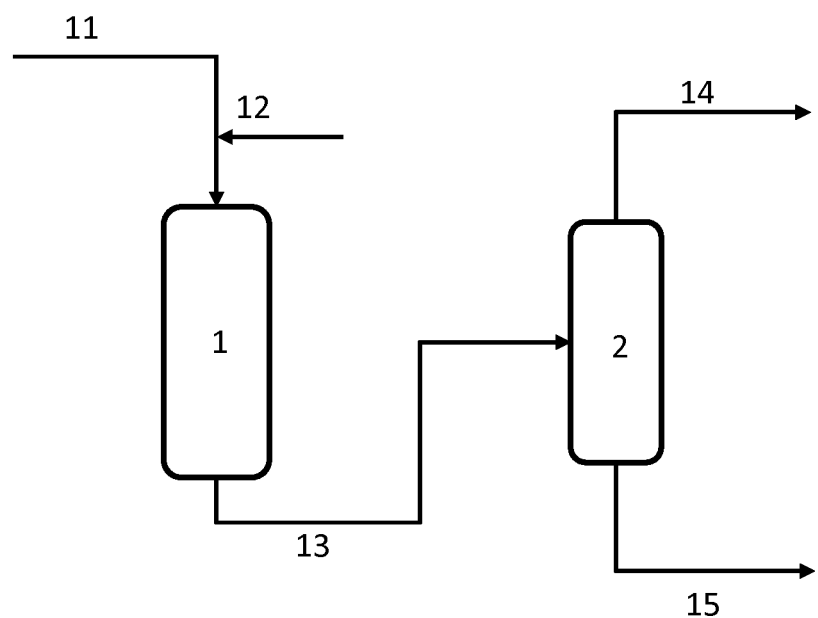

REMOVAL OF BROMINE INDEX-REACTIVE COMPOUNDS

CROSS REFERENCE TO RELATED APPLICATIONS

This application claims priority to and the benefit of U.S. Ser. No. 61/912,881, filed on Dec. 6, 2013, the disclosure of which is incorporated herein by reference in its entirety.

FIELD OF THE INVENTION

The invention relates to a process for the removal of Bromine Index-reactive compounds from aromatic-containing hydrocarbon streams.

BACKGROUND OF THE INVENTION

Olefinic impurities are commonly found in aromatic-containing hydrocarbon streams derived from various sources, such as petroleum fractionation, reforming, thermal cracking, catalytic cracking, isomerization, transalkylation, alkylation, coking, conversion of oxygenates, conversion of biomass, etc. For example, it is well known that aromatic streams derived from reforming often contain olefinic impurities including mono-olefins, di-olefins, and styrenic compounds such as styrene, di-vinylbenzene, etc. It has also been discovered recently that xylenes produced by alkylating toluene and/or benzene with an alkylating agent comprising methanol and/or DME over a solid acid catalyst contain small quantities of styrene. See U.S. Patent Publication No. 2013-0324779.

Olefinic impurities in aromatic-containing hydrocarbon streams are commonly quantified in terms of Bromine Index (BI) based on ASTM D-2710-92, according to which BI is a measure of milligrams of bromine consumed by 100 grams of sample under given conditions. Following this convention, it is a common practice to define such olefinic impurities as BI-reactive compounds and to measure the removal of the olefinic impurities in terms of BI removal.

Aromatic-containing hydrocarbons are valuable feedstocks for the manufacturing of many important commercial products, including synthetic fibers, plastics, synthetic rubbers, lubricants, dyes, detergents, drugs, explosives, pesticides, etc. However, the BI-reactive impurities are removed from the aromatic streams prior to the manufacturing processes for several reasons. Without intending to provide a comprehensive list of such reasons, one reason is to prevent side reactions that could lead to poor product quality and/or undesirable co-products. The removal is also important for protecting downstream processes and/or equipment. For example, molecular sieves are used as adsorbents for separating xylene isomers to recover high purity para-xylene (PX), which is useful in the manufacture of synthetic fibers and resins. BI-reactive compounds, even present in trace quantities, could reduce the adsorption capacity of molecular sieves for PX, rendering the separation process difficult to operate. It is also known that BI-reactive compounds could cause fouling in high temperature equipment such as the reboilers of some fractionation columns.

Conventionally, BI-reactive compounds in aromatic-containing hydrocarbons are removed using a fixed-bed treatment, in which the hydrocarbon stream is flowed through one or more than one vessel or bed loaded with clays, molecular sieves, or a combination thereof, at appropriate temperatures and sufficient pressures to maintain a liquid phase operation. The clays and/or molecular sieves may work as catalysts to oligomerize/polymerize the BI-reactive impurities to form heavy olefinic compounds. They may also promote the alkylation of BI-reactive impurities onto aromatic compounds to form heavy alkylated aromatic compounds. Because some of the resulting heavy compounds would remain in the liquid streams, the clay/molecular sieve treatment is typically followed by a fractionation treatment to separate the resulting heavy compounds from the lighter hydrocarbons.

Some of the heavy compounds, however, could deposit on the clays and/or the molecular sieves. It is also possible that the clays and/or the molecular sieves could permanently adsorb some of the BI-reactive impurities. Such deposition and permanent adsorption would deactivate the clays and/or molecular sieves and reduce their BI-removal capability. When the deactivation reaches to a point that the clays/molecular sieves can no longer meet the design BI removal target, the clays and/or molecular sieves will need to be replaced or regenerated. The time it takes to reach such a point is known as the run length. At that point, the clays and/or molecular sieves would need to be unloaded and replaced with fresh materials. The spent clays and/or molecular sieves would be disposed of as solid wastes or they may be regenerated. Both disposal and regeneration are costly. Short run lengths and frequent generation of large amounts of solid wastes are detrimental to manufacturing plants and the environment.

U.S. Pat. No. 2,778,863 teaches a process for removing BI-reactive impurities from hydrocarbons streams containing $C_6$ and $C_7$ aromatics by contacting the hydrocarbons with a well-known polymerizing clays, e.g., bentonite clay, Attapulgus clay, Fuller's earth, Superfiltrol, Floridin, etc. The run lengths of the clay bed are only in the range of 40 to 60 days. At that point, the clay bed would need to be replaced with fresh clay.

U.S. Pat. No. 4,795,550 teaches removing trace quantities of BI-reactive impurities from hydrocarbon streams containing substantially aromatic and naphthenic hydrocarbons by contacting the streams with a solid medium comprising a crystalline aluminosilicate zeolite and a refractory inorganic oxide. Faujasite is mentioned as a preferred aluminosilicate zeolite and the refractory inorganic oxide can be alumina, silica-alumina, or a mixture of both. It was disclosed that such a solid medium removed BI-reactive impurities more efficiently and to a greater degree without the high levels of deleterious transalkylation by-products attributable to the clay-treating process. However, it was silent on the run lengths of the solid medium.

U.S. Pat. No. 6,368,496 discloses that BI-reactive impurities would rapidly deactivate both clay and molecular sieves in aromatics treatment services, leading to very limited run lengths. In an attempt to achieve longer run lengths, it teaches a two-step treatment of which the first step is to pretreat the aromatic stream to remove dienes (di-olefins) by contacting it with clay or a hydrotreating catalyst to generate a diene-free stream, which is followed by the second step of removing mono-olefin impurities from the diene-free stream by contacting it with an acidic catalyst, preferably a crystalline molecular sieve having ten or more membered oxygen rings, such as large pore zeolites, MCM-22 type materials, etc. The two-step treatment was based on the consideration that dienes are prone to catalyst deactivation. Therefore, removing the highly reactive dienes over a low-cost clay in the first step treatment would improve the run lengths of the more expensive molecular sieve in the second step. This approach suffers from the disadvantages that a two-step treatment is usually more expensive than a one-step treatment in terms of investments and operating costs, and that the clay or the hydrotreating catalyst in the first step, working specifically on the highly reactive dienes, would still suffer from the problems of short run lengths and consequently frequent generations of solid wastes.

It is important to point out that U.S. Pat. No. 6,368,496 specifically teaches not to add any hydrogen in the first-step treatment, regardless whether a clay or a metal-containing hydrogenation or hydrotreating catalysts is used. It further teaches that the aromatic stream after the first-step treatment is treated directly over an acidic catalyst in the second-step treatment to substantially remove the mono-olefins, apparently without adding any hydrogen as well. Such a teaching of not adding any hydrogen is understandable because the conventional ways of introducing hydrogen gas such as in conventional hydrotreating processes typically involve hydrogen separation, recompression, and recycle, which are complex and costly.

As far as the present inventors are aware, the prior art has not been able to address satisfactorily the problems of short run length and frequent generation of solid wastes associated with clay and/or molecular sieve treatments.

SUMMARY OF THE INVENTION

The present inventors have surprisingly discovered a process for improving the run lengths of the clay bed(s) and/or the molecular sieve bed(s) for removing BI-reactive impurities from aromatic-containing hydrocarbon streams. The process significantly reduces the generation of solid wastes and increases the removal efficiency.

The invention is directed to the use of dissolved hydrogen in a purification process for the removal of Bromine Index (BI)-reactive compounds from an aromatic-containing hydrocarbon stream derived from various sources, such as petroleum fractionation, reforming, thermal cracking, catalytic cracking, isomerization, transalkylation, alkylation, coking, conversion of oxygenates, conversion of biomass, etc. The purification process comprises contacting the aromatic-containing hydrocarbon stream in the liquid phase in the presence of dissolved hydrogen with at least one suitable catalytic material under conditions effective to provide a product stream having a lower concentration of BI-reactive compounds than the untreated stream. Depending on the BI level of said stream, the hydrogen dissolved in the liquid stream may be present in the concentration range of 1 to 100 wppm (weight ppm), such as 1 to 50 wppm, or 1 to 20 wppm, based on the total weight of the aromatic-containing hydrocarbons. Preferably, the contact occurs in the temperature range of 40° C. to 350° C., more preferably 100° C. to 300° C.

Preferably, the aromatic-containing hydrocarbon product stream may be subjected to additional processing steps such as fractionation, adsorptive separation, extraction, crystallization, membrane separation, and the like, to remove the species produced in said purification process and/or to recover other components in said product stream. In a preferred embodiment, the amount of BI-reactive compounds removed in said purification process is greater than the amount of benzene produced in said process, and/or greater than the amount of para-xylene (PX) isomerization that occurs in said process.

It is an object of the invention to provide a continuous, semi-continuous, or batch process of purifying aromatic-containing hydrocarbon streams of BI-reactive impurities with extended run lengths and reduced generation of solid wastes as well as with minimal co-production of benzene and minimal isomerization of PX to another $C_8$ aromatic isomer. It is another object of the invention to provide an apparatus adapted for the process of the invention. These and other objects, features, and advantages will become apparent as reference is made to the following detailed description, preferred embodiments, examples, and appended claims.

BRIEF DESCRIPTION OF THE DRAWINGS

FIG. 1 is a schematic diagram showing a preferred embodiment of the present invention.

DETAILED DESCRIPTION OF THE INVENTION

The invention is directed to a purification process for removing BI-reactive compounds from an aromatic-containing hydrocarbon stream by contacting in liquid phase in the presence of dissolved hydrogen at least one appropriate catalytic material under conditions sufficient to reduce the amount of BI-reactive compounds over a run length longer than that possible in the absence of dissolved hydrogen, without producing significant amount benzene and/or isomerization of para-xylene (PX). More particularly, para-xylene loss to isomerization by said contact is less than 5 wt %, or less than 3 wt %, or less than 2 wt %, or less than 1 wt %, or less than 0.6 wt %. The invention is also directed to an apparatus for performing the process.

For the purposes of this invention, the phrase "BI-reactive compounds" means hydrocarbon contaminants containing olefinic bonds, principally dienes and mono-olefins, and which are quantified by the Bromine Index (BI). BI is a well-known indicator of the presence of olefinic bonds. It is often determined according to ASTM D 2710-92. See, for example, U.S. Pat. No. 6,368,496.

Without wishing to be bound by theory, it is possible that the BI-reactive compounds and some of the aromatic compounds in the aromatic-containing hydrocarbon feedstream are being converted to heavy products, such as heavy olefinic compounds, heavy aromatic compounds, or mixtures thereof, over the catalytic materials through reactions such as one or more of oligomerization, polymerization, alkylation, transalkylation, and other hydrocarbon conversion processes. The heavy products may then be removed downstream, such as by distillation, filtration, and the like, resulting in an overall removal of BI-reactive compounds from the aromatic-containing hydrocarbon stream. If a clay is used as the catalytic material it would have to be replaced at the end of the run length because clays are not practically regenerable, and thus, solid wastes need to be disposed of. If a molecular sieve such as MCM-22 is used, it may be regenerated at the end of the run length with a coke burn, which contributes to $CO_2$ emission. Thus, regardless of the catalytic materials used, short run lengths are detrimental to manufacturing plants and the environment.

Surprisingly, dissolved hydrogen, even at less than 100 wppm (weight ppm) levels, is able to maintain the activity of the catalytic materials to achieve longer run lengths by reducing the deposition of heavy products and/or the permanent adsorption of BI-reactive compounds on the catalytic materials. The improvement can be realized even for catalytic materials that do not contain any significant levels of metal components, or possess any hydrogenation, hydrotreating, or hydroprocessing functions.

The invention may be practiced using aromatic-containing hydrocarbon streams derived from various sources, such as petroleum fractionation, reforming, thermal cracking, catalytic cracking, isomerization, transalkylation, alkylation, coking, conversion of oxygenates, conversion of biomass, etc. For example, when aromatic-containing streams are obtained from reforming and cracking processes, the streams may include, e.g., mononuclear aromatic hydrocarbons and undesirable olefins including styrenic compounds, and the streams have an initial Bromine Index (BI) from about 100 to about 3000. The aromatics include, for example, benzene, toluene, xylene, ethyl benzene, cumene and other aromatics derived, e.g., from reformate. Reformate is separated by distillation into light reformate and heavy reformate. Light reformate is mostly benzene and toluene. Heavy reformate includes toluene, ortho-, meta-, and para-xylenes and other heavier aromatics including $C_9^+$. The aromatic streams to be treated according to the invention contain BI-reactive compounds in levels which interfere in subsequent aromatics processing. Depending on the locations in a reforming process, reformate streams typically contain BI-reactive compounds in the range of 0.05 to about 1.5 weight percent or a BI from about 100 to about 3000. Using the method of the invention, the BI-reactive contaminants in such aromatic streams can be decreased to a level which does not interfere in subsequent aromatics processing over a longer run length.

The invention may also be practiced using aromatic-containing streams obtained from alkylation, such as using a feedstock of benzene, toluene, or any combination thereof, as the aromatic species to be alkylated, and a feedstock of methanol, dimethylether (DME), and any combination thereof, as the alkylating agent to produce an aromatic-containing hydrocarbon stream. A typical composition of the aromatic-containing stream produced from the reaction of toluene with methanol in the presence of a solid acid catalyst is shown in Table 1. The presence of styrene would be detrimental to downstream PX recovery operations. The invention can convert styrene in said aromatic-containing stream to a heavy aromatic product (e.g., $C_9^+$ aromatics) by using said catalytic material in liquid phase in the presence of dissolved hydrogen under appropriate conditions to reduce the amount of styrene without production of significant amounts of benzene or isomerization of PX. Further, the invention can do so over longer run lengths than in the absence of dissolved hydrogen. The heavy product can then be removed in downstream distillation.

TABLE 1

| Compound | wt % |
| --- | --- |
| $C_7$ Aromatics | 0.1 |
| Styrene | 0.1 |
| $C_8$ Aromatics | 95.0 |
| $C_9^+$ Aromatics | 4.7 |
| Non Aromatics | 0.1 |
| Oxygenates | trace |

The invention may also be practiced using aromatic-containing streams obtained from conversion of oxygenates. Such streams include, but are not limited to, the following: methanol to olefins; methanol to aromatics; methanol to gasoline; ethanol to olefins; ethanol to aromatics; ethanol to gasoline; synthetic gas to olefins; synthetic gas to aromatics; and synthetic gas to liquid hydrocarbons.

The invention may be better understood by reference to FIG. 1, which is a schematic illustration of a preferred embodiment of the invention. One of skill in the art in possession of the present discourse will understand that the invention may be practiced other than as specifically illustrated in FIG. 1, and the illustration is not intended to be limiting.

In FIG. 1, an aromatic-containing hydrocarbon stream is fed through conduit 11 in liquid phase to apparatus 1, which comprises at least one reactor suitable for contacting the aromatic-containing hydrocarbon stream with at least one catalytic material to convert the BI-reactive compounds in the stream to heavy products. Apparatus 1 may be of any type of reactor such as fixed-bed, fluid-bed, adiabatic, isothermal, etc., in any configuration which is effective in achieving the desired degree of removal. It may utilize either upward or downward flow, with downward flow being preferred. When an apparatus uses more than one bed and/or more than one reactor, the beds and/or reactors can be staged, connected in series, connected in parallel, or combination thereof. The pressure should be sufficient to maintain liquid-phase conditions.

Hydrogen may be added to the aromatic-containing hydrocarbon stream via conduit 12 and in such a way that all hydrogen added is dissolved into the liquid aromatic-containing hydrocarbons. Although FIG. 1 shows that hydrogen is added prior to the stream entering into apparatus 1, it is possible that hydrogen and the stream are introduced into apparatus 1 simultaneously. Apparatus 1 is operated in two phases, i.e., a solid phase of the catalytic material and a liquid phase of the aromatic-containing hydrocarbons with dissolved hydrogen. The concentration of dissolved hydrogen could be in the range of 1 to 100 wppm, such as 1 to 50 wppm, or 1 to 20 wppm, depending on the BI level of the aromatic-containing hydrocarbon stream. The amount of dissolved hydrogen may be determined by estimating the concentration based on hydrogen solubility or by the amount of hydrogen injected into the hydrocarbon stream. Dissolved hydrogen has many advantages over hydrogen gas such as that employed in conventional hydrotreating or hydroprocessing processes. The advantages include lower hydrogen concentration, no need for expensive hydrogen recompression and recycle, lower costs due to fewer pieces of processing equipment, better flow distribution and more effective contact inside apparatus 1.

One of the ways to obtain dissolved hydrogen is to control the addition rate of hydrogen so that all hydrogen added to the liquid aromatic-containing stream is dissolved. Hydrogen can be dissolved in a liquid hydrocarbon stream as long as the concentration of hydrogen is at or below the hydrogen solubility of the liquid hydrocarbon. Anyone skilled in the art can calculate the hydrogen rate easily based on the hydrogen solubility of the liquid hydrocarbon. Thus, in a preferred embodiment the contacting of the aromatic hydrocarbon stream comprising dissolved hydrogen is strictly two-phase: the liquid (with dissolved hydrogen) and the solid catalyst for BI-reduction. Optionally, equipment such as flow controller, inline mixer, orifice, pump, valve, tank, etc., can be used to help the dissolution of hydrogen in the liquid aromatic-containing hydrocarbon stream. Apparatus for hydrogen compression and/or hydrogen recycle, such as would be advantageous if not required in the case of hydrogen gas being present, are not necessary and in preferred embodiments are not present or at least are not in fluid communication with the vessel used for contacting of the aromatic hydrocarbon liquid with the BI-reduction solid.

In accordance with the present invention, apparatus 1 may be operated at suitable conversion conditions to convert the BI-reactive compounds to heavy products, which can be determined by one of ordinary skill in the art. Examples of these conversion conditions, which should be taken as representative and not limiting, include a temperature of from about 40° C. to about 350° C., a pressure of from about 100 kPa to about 7000 kPa and a weight hourly space velocity (WHSV) of between about 0.1 and about 200 hr$^{-1}$. Preferably, the conversion conditions may include a temperature of from about 100° C. to about 300° C., a pressure of from about 200 kPa to about 5000 kPa and a WHSV of between about 0.5 and about 50 hr$^{-1}$. The WHSV is based on the weight of catalyst composition, i.e., the total weight of active catalytic material plus any binder that is used.

In accordance with the present invention, apparatus 1 may be operated initially at a start-up temperature which is a minimum temperature required for a catalytic material to function properly for converting the BI-reactive compounds to heavy products. The temperature may then increase in a positive relation to the quantity of hydrocarbons which have been processed over the catalytic material.

Optionally, the product effluent from apparatus 1 is passed via conduit 13 to a fractionation column 2 wherein the stream is split into an overhead stream, which has less BI-reactive compounds than the aromatic hydrocarbon stream, for downstream processing through conduit 14 and a bottom stream rich in heavy products which is passed downstream through conduit 15.

Catalytic material suitable for removal of BI-reactive compounds according to the present invention, for example in apparatus 1 in FIG. 1, may include members of hydrotreating catalysts, which may have a metal component. Nonlimiting examples of the metal include a single metal from Groups 3 (Scandium Group, including Lanthanides and Actinides) to 12 (Zinc Group) of the Periodic Table, such as nickel, cobalt, chromium, vanadium, molybdenum, tungsten, or a combination of metals such as nickel-molybdenum, cobalt-nickel-molybdenum, cobalt-molybdenum, nickel-tungsten or nickel-tungsten-titanium. Generally, the metal component is selected for good hydrogen transfer activity and the catalyst as a whole should have good hydrogen transfer and minimal cracking characteristics. A preferred hydrotreating catalyst is a commercial NiMo/Al$_2$O$_3$ catalyst, such as HDN-60, manufactured by American Cyanamid. The catalyst is used as it is received from the manufacturer, i.e., in its oxide form. The support for the catalyst is conventionally a porous solid, usually alumina, or silica-alumina. However, other porous solids such as magnesia, titania or silica, either alone or mixed with alumina or silica-alumina may also be used, as convenient. A preferred hydrotreating catalyst is a nickel molybdenum/alumina.

Other suitable catalytic materials suitable for removal of BI-reactive compounds according to the present invention are molecular sieves having a pore size appropriate to catalyze the desired conversion. The molecular sieve useful for the conversion of this invention is usually a large pore size molecular sieve having a silica-to-alumina molar ratio of at least about 2, specifically from about 2 to 100. The silica to alumina ratio is determined by conventional analysis. This ratio is meant to represent, as closely as possible, the molar ratio in the rigid anionic framework of the molecular sieve crystal and to exclude silicon and aluminum in the binder or in cationic or other form within the channels.

Molecular sieves are divided into three major groups, according to their pore/channel systems. These three major systems include 8-membered oxygen ring systems, 10-membered oxygen ring systems and 12-membered oxygen ring systems. In general, they are referred to as small, medium or large pore-size molecular sieves proceeding from 8 to 12 membered systems. There are also dual pore systems including 10 and 12 membered oxygen ring systems. These systems are more completely described in Atlas of Zeolite Structure Types, International Zeolite Assoc., Polycrystal Book Service, Plattsburg, 1978.

The chemical composition of molecular sieves can vary widely. Typically, molecular sieves consist of SiO$_2$ structures, in which some of the silicon atoms are replaced members of the Periodic Table of Elements such as by tetravalent ions (such as Ti or Ge), trivalent ions (such as Al, B, Ga, Fe, bivalent ions such as Be), or a combination thereof. When there is substitution by bivalent or trivalent ions, cations such as Na$^+$, Ca$^{+2}$, NH$_4^+$ or H$^+$ are present in the as-synthesized molecular sieve structure, along with organic ions such as tetramethylamine (TMA$^+$), tetraethylamine (TEA$^+$) and others. The organics are typically removed by calcination before the molecular sieve is used. Ion exchange of residual cations with, for example, NH$_4^+$, is generally followed by calcination to produce the acidic molecular sieve.

Preferred molecular sieves for the inventive process include natural or synthetic crystalline molecular sieves, with ring structures of ten to twelve members or greater. Crystalline molecular sieves useful as catalytic materials include as non-limiting examples, large pore zeolites ZSM-4 (omega) (U.S. Pat. No. 3,923,639); mordenite, ZSM-12, ZSM-18 (U.S. Pat. No. 3,950,496); ZSM-20 (U.S. Pat. No. 3,972,983); zeolite Beta (U.S. Pat. Nos. 3,308,069 and Re 28,341); Faujasite X (U.S. Pat. No. 2,882,244); Faujasite Y (U.S. Pat. No. 3,130,007); USY (U.S. Pat. Nos. 3,293,192 and 3,449,070); REY and other forms of X and Y, MCM-22 (U.S. Pat. No. 4,954,325); MCM-36 (U.S. Pat. No. 5,229,341); MCM-49 (U.S. Pat. No. 5,236,575); MCM-56 (U.S. Pat. No. 5,362,697); and mesoporous materials, such as M41S (U.S. Pat. No. 5,102,643) and MCM-41 (U.S. Pat. No. 5,098,684). More preferred molecular sieves include 12 membered oxygen-ring structures ZSM-12, mordenite, zeolite Beta, USY, and the mixed 10-12 membered oxygen ring structures from the MCM-22 family, layered materials, and mesoporous materials. Most preferred are the MWW family of molecular sieves, which include, MCM-22, MCM-36, MCM-49, MCM-56, and EMM-10. The MCM-22 type materials may be considered to contain a similar common layered structure unit. The structure unit is described in U.S. Pat. Nos. 5,371,310; 5,453,554; 5,493,065; and 5,557,024. Each of the patents in this paragraph describing molecular sieve materials is herein incorporated by reference.

One measure of the acid activity of a zeolite is the Alpha Value. The Alpha Value is an approximate indication of the catalyst acid activity and it gives the relative rate constant (rate of normal hexane conversion per volume of catalyst per unit time). It is based on the activity of the highly active silica-alumina cracking catalyst taken as an Alpha of 1 (Rate Constant=0.16 sec$^{-1}$). The alpha test is described in U.S. Pat. No. 3,354,078 in the Journal of Catalysis, Vol. 4, p. 527 (1965); Vol. 6, p. 278, and Vol. 61, p. 395 (1980), each of which is herein incorporated by reference as to that description. The experimental conditions of the test used include a constant temperature of 538° C., and a variable flow rate as described in the Journal of Catalysis, Vol. 61, p. 395 (1980). The catalytic materials suitable for the present invention may have an Alpha Value from about 100 to about 1000.

The crystalline molecular sieve may be used in bound form, that is, composited with a matrix material, including synthetic and naturally occurring substances, such as clay, silica, alumina, zirconia, titania, silica-alumina and other metal oxides. Naturally-occurring clays include those of the montmorillonite and kaolin families. The matrix itself may possess catalytic properties, often of an acidic nature. Other porous matrix materials include silica-magnesia, silica-zirconia, silica-thoria, silica-beryllia, silica-titania, as well as ternary compositions such as silica-alumina-thoria, silica-alumina-zirconia, silica-alumina-magnesia, and silica-alumina-zirconia. A mixture of these components can also be used. The relative proportions of crystalline molecular sieve material and matrix can vary widely from 1 to 90 weight percent, usually about 20 to about 80 weight percent. The molecular sieve can also be used in the absence of matrix or binder, i.e., in self-bound or unbound form. The catalyst can be used in the form of extrudate (e.g., lobed form such as trilobe), sphere, or powder.

Suitable catalytic materials that can be used for removal of BI-reactive compounds according to the present invention may also include members of refractory oxides, clays, and mixtures thereof. The material may be naturally occurring material, such as bauxite or mordenite clay, or a synthetic material and may comprise alumina, silica, aluminosilicate, titania, magnesia or zirconia or some other compound which exhibits similar properties. Many types of clays are available commercially and are suitable for use in the present invention, including Engelhard F-24 clay, Filtrol Corporation's Superfiltrol, Filtrol 24, Filtrol 25 and Filtrol 62 clays, Fuller's earth, Floridin clay, Attapulgus clay, and Tonsil clay. In a preferred embodiment, the clays are pretreated with acids such as HCl, $H_3PO_4$, or $H_2SO_4$ acid.

In order to more fully understand the present invention, the following detailed experiments are described. It will be understood that the experiments are not intended to be limiting but that the invention can be practiced otherwise than specifically described.

Example 1

A reactor containing a catalyst of self-bound 100% MCM-22 was fed an aromatic-containing hydrocarbon stream comprising mainly xylenes as well as 1000 wppm styrene and 1000 wppm octene-2 at 7 WHSV and 265 psig (1827 kPa). No hydrogen was present. The stream had a BI of 300. The target was to reduce the BI from 300 to 20. Product collected at the outlet was analyzed with gas chromatography (GC) and BI measurement. Reactor temperatures and removal results are presented as functions of time on stream and sampling time in Table 2, respectively. It is seen that at the start-up temperature of 180° C., the catalyst was able to reduce the BI in product to about 12 up to about 318 hours. However, the catalyst lost its activity rapidly as BI in product increased from 12 to 131 between 318 to 1323 hours. From 1323 to about 4926 hours, it was necessary to raise the reactor temperature from 180° C. to the maximum temperature of 265° C. to keep the product BI below the level of 20. Because the reactor had reached its upper temperature limit, the catalyst would have to be replaced once the BI rose above the target of BI 20, which gave a run length of slightly more than 4926 hours with respect to the hydrocarbon stream used.

TABLE 2

| Time on Stream, Hours | Temperature, ° C. | Sampling Time, Hours | BI in Product Samples |
|---|---|---|---|
| 0-318 | 180 | 318 | 12 |
| 318-1323 | 180 | 1275 | 131 |
| 1323-1467 | 200 | 1467 | 58 |
| 1467-1850 | 220 | 1850 | 35 |
| 1850-1995 | 230 | 1995 | 24 |
| 1995-2693 | 240 | 2693 | 12 |

TABLE 2-continued

| Time on Stream, Hours | Temperature, ° C. | Sampling Time, Hours | BI in Product Samples |
|---|---|---|---|
| 2693-4806 | 250 | 4758 | 34 |
| 4806-4926 | 265 | 4926 | 15 |

Example 2

The test in Example 1 was repeated with a fresh self-bound MCM-22 catalyst. The feed stream had the same composition as that used in Example 1 with the exception that 15 wppm $H_2$ was added to the feed in the form of dissolved $H_2$. Reactor temperatures and removal results are presented as functions of time on stream and sampling time in Table 3, respectively. It is seen that at the start-up temperature of 180° C., the catalyst was able to reduce the BI in the product to about 14 from 0 to about 1895 hours, which was a much better performance than without dissolved $H_2$ in feed as shown in Example 1. Even though the BI in product was below the target of 20, the reactor temperature was adjusted from 1895 hours to simply observe the effects of temperature. From 1895 to 4514 hours, the reactor temperature was raised from 180° C. to only 230° C. and the product BI at well below the target of 20 throughout. The facts that at 230° C. the product BI was 2, which was well below the target BI of 20, and that 230° C. was far from the reactor temperature limit of 265° C. clearly showed that the catalyst with 15 wppm of dissolved $H_2$ in feed could be operated well beyond the run length of 4926 hours observed in Example 1. In addition, the product showed less than 50 wppm benzene and less than 1% xylene isomerization, indicating that the dissolved $H_2$ did not produce any significant undesirable reactions.

TABLE 3

| Time on Stream, Hours | Temperature, ° C. | Sampling Time, Hours | BI in Product Samples |
|---|---|---|---|
| 0-1895 | 180 | 1895 | 14 |
| 1895-2670 | 190 | 2591 | 14 |
| 2670-3098 | 210 | 3098 | 7 |
| 3098-4514 | 230 | 4514 | 2 |

The present invention can be integrated with other systems using toluene and benzene streams, such as selective alkylation of benzene and/or toluene, disproportionation of toluene, and/or transalkylation of toluene and aromatic $C_9^+$ species.

The invention has been described above with reference to numerous embodiments and specific examples. Many variations will suggest themselves to those skilled in this art in light of the above detailed description.

All patents and patent applications, test procedures (such as ASTM methods and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

What is claimed is:

1. A process for the removal of Bromine Index (BI)-reactive compounds from an aromatic-containing hydrocarbon stream, the process comprising:

contacting said aromatic-containing hydrocarbon stream in a liquid phase with at least one solid material selected from molecular sieves, clays, refractory oxides, and mixtures thereof, wherein the at least one solid material does not possess a hydrogenation function, the aromatic-containing hydrocarbon stream comprises para-xylene, BI-reactive compounds comprising styrene, and hydrogen that is dissolved into the aromatic-containing hydrocarbon stream, the concentration of said dissolved hydrogen is in a range of 1 to 100 wppm based on the total weight of the aromatic-containing hydrocarbon stream, and said contacting occurs at a temperature range of 40° C. to 350° C., at pressures sufficient to maintain liquid phase;

wherein the contacting converts at least some of the BI-reactive compounds into heavier products including $C_9^+$ aromatic hydrocarbons in the presence of the dissolved hydrogen, wherein the para-xylene loss to isomerization is less than 5 wt %, and wherein the contacting produces 100 wppm or less benzene, based on the total amount of aromatic hydrocarbon; and producing a product stream from the contacting, the product stream comprising the heavier products and having a lower concentration of BI-reactive compounds than the aromatic-containing hydrocarbon stream.

2. The process of claim 1, wherein the concentration of said dissolved hydrogen is in a range of 1 to 50 wppm based on the total weight of the aromatic-containing hydrocarbon stream.

3. The process of claim 1, wherein the concentration of said dissolved hydrogen is in a range of 1 to 20 wppm based on the total weight of the aromatic-containing hydrocarbon stream.

4. The process of claim 1, wherein said dissolved hydrogen is added to said aromatic-containing hydrocarbon stream prior to said contact using at least one apparatus selected from flow controller, valve, inline mixer, orifice, pump, and tank.

5. The process of claim 1, wherein said aromatic-containing hydrocarbon stream comprises an effluent downstream of at least one process selected from reforming, isomerization, alkylation, disproportionation, transalkylation, catalytic cracking, steam cracking, coking, conversion of oxygenates, and conversion of biomass.

6. The process of claim 5, wherein said aromatic-containing hydrocarbon stream comprises an effluent downstream of an alkylation process comprising a reaction of an alkylating agent selected from methanol, DME, and mixtures thereof, with benzene and/or toluene in the presence of a suitable alkylation catalyst under appropriate conditions to provide said process stream.

7. The process of claim 5, wherein said aromatic-containing hydrocarbon stream comprises an effluent downstream of an oxygenate conversion process selected from methanol to olefins, methanol to aromatics, methanol to gasoline, ethanol to olefins, ethanol to aromatics, ethanol to gasoline, synthetic gas to olefins, synthetic gas to aromatics, and synthetic gas to liquid hydrocarbons.

8. The process of claim 1, wherein said product stream is subjected to at least one additional process selected from fractionation, crystallization, extraction, and adsorptive separations.

9. The process of claim 8, wherein said product stream is subjected to at least one fractionation to separate heavy products from said product stream.

10. The process of claim 1, wherein more than 90 wt % of said BI-reactive compounds are removed from said stream.

11. The process of claim 1, wherein the at least one solid material is selected from the following group of molecular sieves: ZSM-4, mordenite, ZSM-12, ZSM-18, ZSM-20, zeolite Beta, Faujasite X, Faujasite Y, USY, REY, MCM-22, MCM-36, MCM-49, MCM-56, M41S, MCM-41, and mixtures thereof.

12. The process of claim 1, wherein the at least one solid material is selected from the following group of clays: bauxite clay, mordenite clay, Engelhard F-24 clay, Filtrol 24 clay, Filtrol 25 clay, Filtrol 62 clay, bentonite clay, Fuller's earth, Floridin clay, Attapulgus clay, Tonsil clay, and mixtures thereof.

13. The process of claim 12, wherein said clays are pretreated with HCl, $H_3PO_4$, or $H_2SO_4$ acid.

14. The process of claim 1, wherein the at least one solid material is selected from the following group of refractory oxides: alumina, silica-alumina, magnesia, thoria, beryllia, titania, zirconia, and mixtures thereof.

15. The process of claim 1, wherein the para-xylene loss to isomerization by said contact is less than 0.6 wt %.

* * * * *